(12) United States Patent
Kim et al.

(10) Patent No.: US 11,286,216 B2
(45) Date of Patent: Mar. 29, 2022

(54) METHOD FOR PREPARING ETHYLENE AND APPARATUS FOR PREPARING ETHYLENE

(71) Applicant: LG CHEM, LTD., Seoul (KR)

(72) Inventors: Tae Woo Kim, Daejeon (KR); In Seop Kim, Daejeon (KR); Sung Kyu Lee, Daejeon (KR); Joon Ho Shin, Daejeon (KR); Yeon Uk Choo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 205 days.

(21) Appl. No.: 16/648,541

(22) PCT Filed: Jul. 15, 2019

(86) PCT No.: PCT/KR2019/008708
§ 371 (c)(1),
(2) Date: Mar. 19, 2020

(87) PCT Pub. No.: WO2020/050487
PCT Pub. Date: Mar. 12, 2020

(65) Prior Publication Data
US 2021/0363074 A1  Nov. 25, 2021

(30) Foreign Application Priority Data

Sep. 4, 2018 (KR) .................. 10-2018-0105163
Jul. 3, 2019 (KR) .................. 10-2019-0079915

(51) Int. Cl.
*C07C 4/02* (2006.01)
*C07C 7/00* (2006.01)
*C07C 7/09* (2006.01)

(52) U.S. Cl.
CPC ............... *C07C 4/02* (2013.01); *C07C 7/005* (2013.01); *C07C 7/09* (2013.01)

(58) Field of Classification Search
CPC ............. C07C 4/02; C07C 7/005; C07C 7/09
See application file for complete search history.

(56) References Cited

U.S. PATENT DOCUMENTS 2,938,934 A    5/1960  Williams
3,675,435 A *  7/1972  Jackson ............... F25J 3/0233
                                                         62/622
(Continued)

FOREIGN PATENT DOCUMENTS

CN    1112911 A    12/1995
CN    1715260 A    1/2006
(Continued)

*Primary Examiner* — Thuan D Dang
(74) *Attorney, Agent, or Firm* — Dentons US LLP

(57) ABSTRACT

A method for preparing ethylene, including: passing a feed stream containing C1 and C2 hydrocarbon compounds through a first heat exchanger and feeding the feed stream passed through the first heat exchanger to a second gas-liquid separator; feeding a part of a bottom discharge stream of the second gas-liquid separator to a demethanizer, passing an overhead discharge stream of the second gas-liquid separator through a second heat exchanger, feeding the overhead discharge stream of the second gas-liquid separator passed through the second heat exchanger to a third gas-liquid separator; feeding a bottom discharge stream of the third gas-liquid separator to the demethanizer; feeding a bottom discharge stream of the demethanizer to a C2 separator; feeding an overhead discharge stream of the C2 separator to a second compressor; passing a part of a compressed discharge stream of the second compressor through the first heat exchanger and feeding the part of the compressed discharge stream of the second compressor passed through the first heat exchanger to the second compressor as a first circulation flow; passing a part of the compressed discharge stream of the second compressor through the second heat exchanger and feeding the part of (Continued)

the compressed discharge stream of the second compressor passed through the second heat exchanger to a first compressor as a second circulation flow; and feeding a compressed discharge stream of the first compressor to the second compressor, and an apparatus for preparing ethylene for implementing the same.

20 Claims, 2 Drawing Sheets

(56) References Cited

U.S. PATENT DOCUMENTS

| | | |
|---|---|---|
| 5,361,589 A | 11/1994 | Howard et al. |
| 2006/0021379 A1 | 2/2006 | Ronczy |
| 2017/0050900 A1 | 2/2017 | Su |

FOREIGN PATENT DOCUMENTS

| | | |
|---|---|---|
| CN | 1793092 A | 6/2006 |
| CN | 101263215 A | 9/2008 |
| JP | 62-89634 A | 4/1987 |
| JP | 63-156732 A | 6/1988 |
| JP | 6-502416 A | 3/1994 |
| JP | 7-507078 A | 8/1995 |
| JP | 7-258119 A | 10/1995 |
| JP | 2009-510199 A | 3/2009 |
| JP | 2012-529622 A | 11/2012 |
| KR | 0144699 B1 | 4/1998 |
| KR | 10-0230672 B1 | 8/1999 |
| KR | 10-2005-0000382 A | 1/2005 |
| KR | 10-2008-0056104 A | 6/2008 |
| KR | 10-2016-0109699 A | 9/2016 |
| KR | 10-2017-0126650 A | 11/2017 |

* cited by examiner

FIG. 1 - RELATED ART

METHOD FOR PREPARING ETHYLENE AND APPARATUS FOR PREPARING ETHYLENE

CROSS-REFERENCE TO RELATED APPLICATIONS

This application is the U.S. national stage of international Application No. PCT/KR2019/008708, filed on Jul. 15, 2019, and claims the benefit of priority from Korean Patent Application No. 10-2018-0105163, filed on Sep. 4, 2018, and Korean Patent Application No. 10-2019-0079915, filed on Jul. 3, 2019, the disclosures of which are incorporated herein by reference in their entirety.

TECHNICAL FIELD

The present invention relates to an method for preparing ethylene, and more particularly, to an method for preparing ethylene capable of increasing yield of ethylene by preventing an overload due to an increase in production amount when ethylene is produced by a pyrolysis method and an apparatus for preparing ethylene for implementing the same.

BACKGROUND

In general, ethylene has been produced by various methods such as a method of pyrolysis naphtha, ethane, propane, and the like, a method of hydrogenating acetylene, a method of dehydrating alcohol, and the like. Among these methods, in the pyrolysis method, a hydrocarbon compound such as naphtha and the like as a feedstock are input to a furnace, the hydrocarbon compound is subjected to pyrolysis in the furnace, and the pyrolysis product is subjected to cooling, compressing, and purifying.

In recent years, in a pyrolysis method using a hydrocarbon compound such as naphtha and the like as a feedstock, in order to an increase yield of product such as ethylene, a method including a gas phase decomposition step in which ethane, propane, and the like are used as a feedstock in addition to a liquid phase decomposition step in which naphtha is used as a feedstock has been used. Here, as ethane, in a pyrolysis product generated by cracking of naphtha, ethane circulated after purification is used as a feedstock, and as propane, in the pyrolysis product generated by cracking of naphtha, propane circulated after purification is used as a feedstock, or propane introduced from the outside is used as a feedstock. In particular, since propane is cheaper than other feedstocks, it may be easily obtained and the cost of production may be lowered.

Meanwhile, in a case where a gas phase decomposition step using ethane, propane, and the like is added to a naphtha pyrolysis process, it is preferable that processes for cooling, compressing, and purifying the product generated from pyrolysis are added, but only a furnace is added due to a problem such as a space for additionally providing the other processes.

However, in a case where an additional furnace is installed and additional propane is introduced from the outside to be used as a feedstock in the furnace, a difference in cracking yield between the additional propane and existing ethane circulated and reused as a feedstock is very large. In particular, in a case where a proportion of the pyrolysis process in which propane is used as a feedstock is increased, such as a case where an additional furnace using propane as a feedstock is installed, a case where the liquid phase decomposition step in which naphtha is used is interrupted due to maintenance of process equipment, or the like, a content of methane in the product generated by pyrolysis is extremely increased, resulting in an occurrence of an overload in a purification process.

SUMMARY

In order to solve the problems mentioned in the background art, an object of the present invention is to provide an method for preparing ethylene capable of coping with a change in a cracking yield depending on a change in the type of feedstock when ethylene is produced by pyrolysis of naphtha.

That is, an object of the present invention is to provide an method for preparing ethylene capable of coping with a change in a cracking yield depending on a change in the type of feedstock when ethylene is produced by pyrolysis of naphtha so that an additional gas furnace in which a gas phase feedstock is used may be freely installed, and may be individually operated even in a case where the liquid phase decomposition step in which naphtha is used is interrupted due to maintenance of process equipment, and an apparatus for preparing ethylene for implementing the same.

In one general aspect, an method for preparing ethylene includes: passing a feed stream containing C1 and C2 hydrocarbon compounds through a first heat exchanger and feeding the feed stream to a second gas-liquid separator; feeding a part of a bottom discharge stream of the second gas-liquid separator to a deethanizer, passing an overhead discharge stream of the second gas-liquid separator through a second heat exchanger, and feeding the overhead discharge stream of the second gas-liquid separator to a third gas-liquid separator; feeding a bottom discharge stream of the third gas-liquid separator to the demethanizer; feeding a bottom discharge stream of the demethanizer to a C2 separator; feeding an overhead discharge stream of the C2 separator to a second compressor; passing a part of a compressed discharge stream of the second compressor through the first heat exchanger and feeding the part of the compressed discharge stream of the second compressor passed through the first heat exchanger to the second compressor as a first circulation flow; passing a part of the compressed discharge stream of the second compressor through the second heat exchanger and feeding the part of the compressed discharge stream of the second compressor passed through the second heat exchanger to a first compressor as a second circulation flow; and feeding a compressed discharge stream of the first compressor to the second compressor.

In another general aspect, an method for preparing ethylene includes: passing a feed stream containing C1 and C2 hydrocarbon compounds through a first heat exchanger and feeding the feed stream to a second gas-liquid separator; feeding a part of a bottom discharge stream of the second gas-liquid separator to a demethanizer, passing an overhead discharge stream of the second gas-liquid separator through a second heat exchanger, and feeding the overhead discharge stream of the second gas-liquid separator to a third gas-liquid separator; feeding a bottom discharge stream of the third gas-liquid separator to the demethanizer; feeding a bottom discharge stream of the demethanizer to a C2 separator; feeding an overhead discharge stream of the C2 separator to a second compressor; passing a part of a compressed discharge stream of the second compressor through the first heat exchanger and feeding the part of the compressed discharge stream of the second compressor passed through the first heat exchanger to the second compressor as a first circulation flow; passing a part of the compressed discharge stream of the second compressor through the second heat exchanger and feeding the part of the compressed discharge stream of the second compressor passed through the second heat exchanger to a first compressor as a second circulation flow; and feeding a compressed discharge stream of the first compressor to the second compressor, wherein the passing of the part of the compressed discharge stream of the second compressor through the second heat exchanger and the feeding of the part of the compressed discharge stream of the second compressor passed through the second heat exchanger to the first compressor as the second circulation flow is performed only in a case where a content of C1 in the feed stream containing the C1 and C2 hydrocarbon compounds is 35 mole % or more.

In still another general aspect, an apparatus for preparing ethylene includes: a first heat exchanger cooling a feed stream by using a part of a compressed discharge stream of a second compressor as a first refrigerant stream, the part of the compressed discharge stream of the second compressor being a first circulation flow; a second gas-liquid separator performing gas-liquid separation on the cooled feed stream discharged from the first heat exchanger; a second heat exchanger cooling an overhead discharge stream of the second gas-liquid separator by using a part of the compressed discharge stream of the second compressor as a second refrigerant stream, the part of the compressed discharge stream of the second compressor being a second circulation flow; a third gas-liquid separator performing gas-liquid separation on the cooled overhead discharge stream of the second gas-liquid separator discharged from the second heat exchanger; a demethanizer separating methane from a bottom discharge stream of the second gas-liquid separator and a bottom discharge stream of the third gas-liquid separator; a C2 separator separating C2 from a bottom discharge stream of the demethanizer; a first compressor compressing the second circulation flow used as the refrigerant in the second heat exchanger; and a second compressor compressing an overhead discharge stream of the C2 separator, the first circulation flow, and a compressed discharge stream of the first compressor.

In a case where ethylene is produced using the method for preparing ethylene and the apparatus for preparing ethylene according to the present invention, it is possible to cope with a change in a cracking yield depending on a change in the type of feedstock, such that an additional gas furnace in which a gas phase feedstock is used may be freely installed, and may be individually operated even in a case where the liquid phase decomposition step in which naphtha is used is interrupted due to maintenance of process equipment.

DETAILED DESCRIPTION

The terms and words used in the description and claims of the present invention are not to be construed as a general or dictionary meanings but are to be construed as meanings and concepts meeting the technical ideas of the present invention based on a principle that the inventors can appropriately define the concepts of terms in order to describe their own inventions in the best mode.

In the present invention, the term "stream" may mean a flow of a fluid in a process and may also mean a fluid itself flowing through a pipe. Specifically, the "stream" may mean both a fluid itself flowing through a pipe connecting respective apparatuses and a flow of the fluid. In addition, the fluid may mean gas or liquid.

Hereinafter, the present invention will be described in more detail for understanding the present invention.

Figure 2:
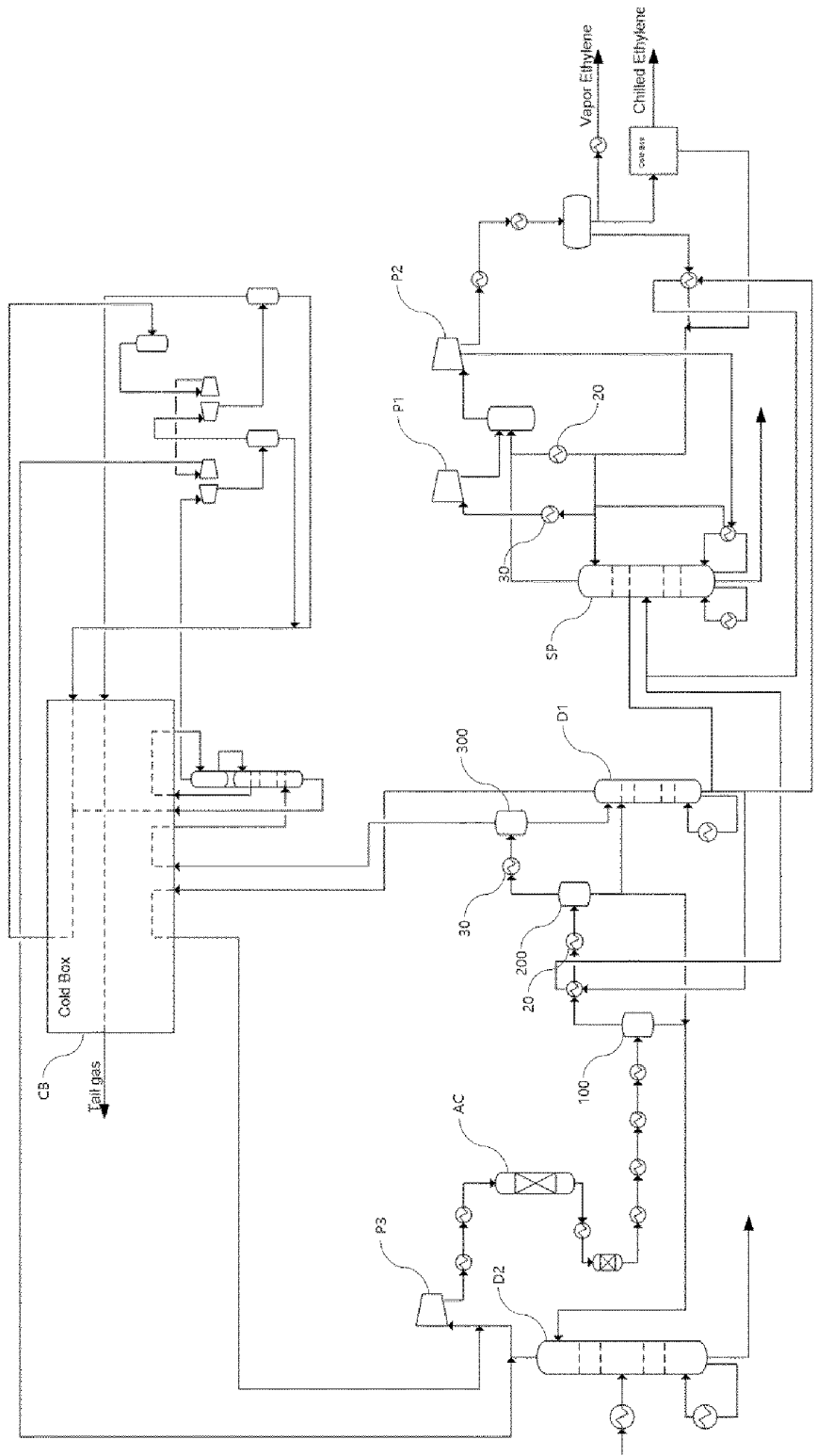
FIG. 2 is a process flow diagram of an method for preparing ethylene according to an embodiment of the present invention.

An method for preparing ethylene according to the present invention may include: a pyrolysis process of inputting naphtha, recycled C2 and C3 hydrocarbon compounds, and propane as a feedstock to respective furnaces and performing pyrolysis in the respective furnaces (S1, not illustrated); a cooling process of cooling pyrolysis gas which is obtained from the pyrolysis in the respective furnaces and contains hydrogen and C1, C2, and C3+ hydrocarbon compounds (S2, not illustrated); a compression process of compressing the cooled pyrolysis gas (S3, not illustrated); and a purification process of purifying a pyrolysis compressed stream containing hydrogen and C1, C2, and C3+ hydrocarbon compounds (S4, illustrated in FIG. 2).

Specifically, the pyrolysis process (S1) may include: a liquid phase decomposition step in which naphtha is used as a feedstock; a gas phase decomposition step in which recycled C2 and C3 hydrocarbon compounds such as ethane, propane, and the like are used as a feedstock; and a gas phase decomposition step in which propane is used as a feedstock.

The cooling process (S2) may include a cooling step of cooling the pyrolysis gas generated in the respective furnaces in the pyrolysis process (S1) in a cooling tower.

The compression process (S3) may include a compression step of compressing the cooled pyrolysis stream in the cooling process (S2) through multistage compression by two or more compressors to purify the cooled pyrolysis stream.

As illustrated in FIG. 2, the purification process (S4) includes: passing a feed stream containing C1 and C2 hydrocarbon compounds through a first heat exchanger 20 and feeding the feed stream to a second gas-liquid separator 200; feeding a part of a bottom discharge stream of the second gas-liquid separator 200 to a demethanizer D1, passing an overhead discharge stream of the second gas-liquid separator 200 through a second heat exchanger 30, and feeding the overhead discharge stream of the second gas-liquid separator 200 to a third gas-liquid separator 300; feeding a bottom discharge stream of the third gas-liquid separator 300 to the demethanizer D1; feeding a bottom discharge stream of the demethanizer D1 to a C2 separator SP; feeding an overhead discharge stream of the C2 separator SP to a second compressor P2; passing a part of a compressed discharge stream of the second compressor P2 through the first heat exchanger 20 and feeding the part of the compressed discharge stream of the second compressor P2 passed through the first heat exchanger 20 to the second compressor P2 as a first circulation flow; passing a part of the compressed discharge stream of the second compressor P2 through the second heat exchanger 30 and feeding the part of the compressed discharge stream of the second compressor P2 passed through the second heat exchanger 30 to a first compressor P1 as a second circulation flow; and feeding a compressed discharge stream of the first compressor P1 to the second compressor P2.

Specifically, in the pyrolysis process (S1), in a case where ethylene is produced through a gas phase decomposition step in which propane is used as a feedstock, since propane is cheaper than other feedstocks, as compared to a case in which naphtha and recycled C2 and C3 hydrocarbon compounds are used as a feedstock, it may be easily obtained from the outside and may be effective in lowering the cost of production and increasing yield of ethylene.

However, in a case of adding propane as a feedstock, as compared to a case where a content of methane in the pyrolysis gas obtained by pyrolysis of recycled ethane which is used as a feedstock is about 10 mole %, a content of methane in the pyrolysis gas generated in the pyrolysis process (S1) is sharply increased to about 20 mole % or more, which is problematic. As such, when the content of methane in the pyrolysis gas is increased, in the purification process (S4), a boiling point of a mixture including hydrogen and a hydrocarbon compound in all streams containing methane is lowered.

Figure 1:
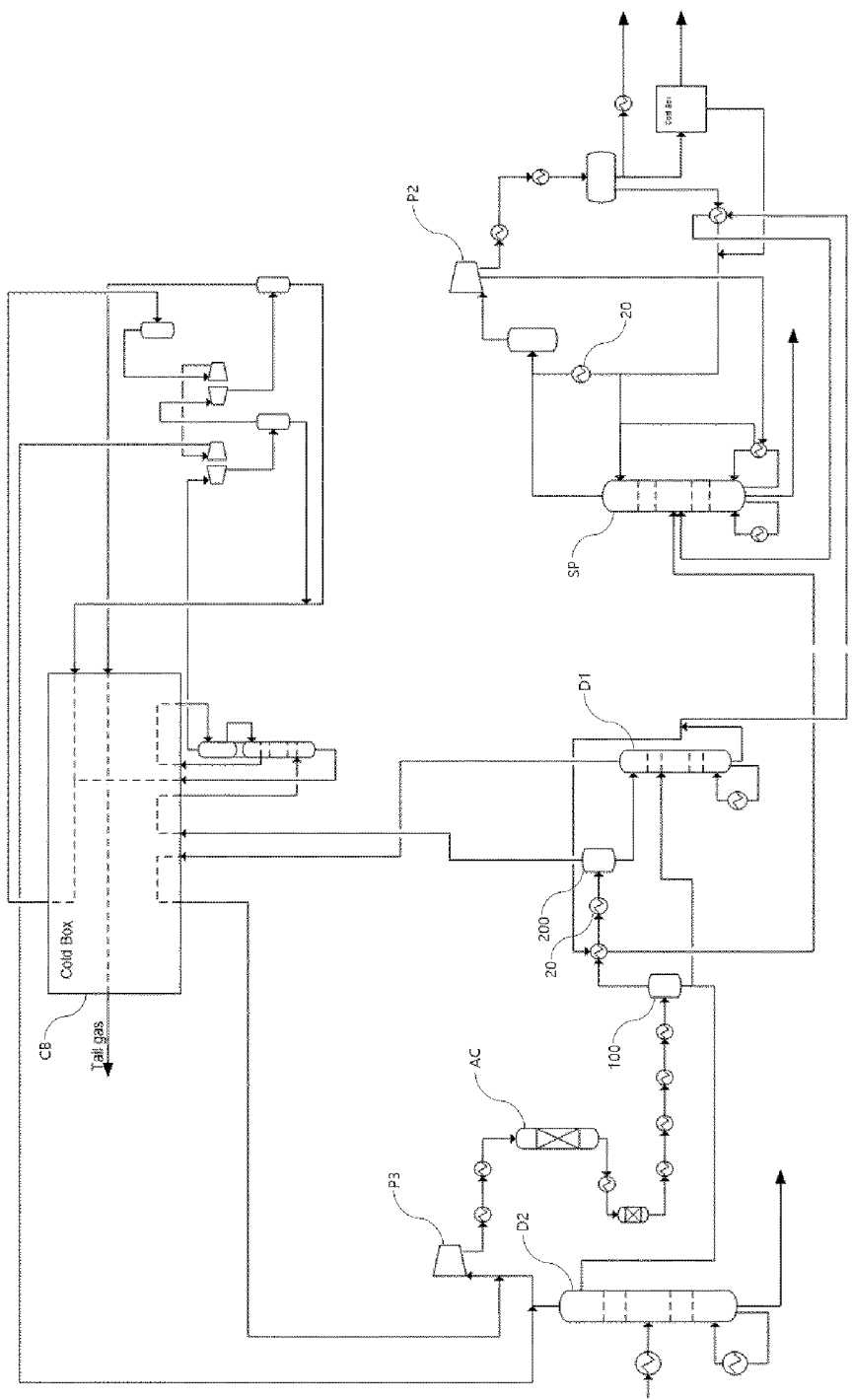
FIG. 1 is a process flow diagram of a method for preparing ethylene according to related art.

Accordingly, as illustrated in FIG. 1, in a case where the second heat exchanger 30 and the third gas-liquid separator 300 are not used, that is in a case where a feed stream containing C1 and C2 hydrocarbon compounds is passed through a first heat exchanger 20 and fed to a second gas-liquid separator 200, a bottom discharge stream of the second gas-liquid separator 200 is fed to a demethanizer D1, a bottom discharge stream of the demethanizer D1 is fed to a C2 separator SP, an overhead discharge stream of the C2 separator SP is fed to a second compressor P2, and a part of a compressed discharge stream of the second compressor P2 is passed through the first heat exchanger 20 and fed to the second compressor SP as a first circulation flow, it is difficult to sufficiently condense the feed stream to be fed to the first heat exchanger 20 with only a refrigerant of the first heat exchanger 20 in a range of −70° C. to −80° C. Therefore, since a flow rate of an overhead discharge stream of the second gas-liquid separator 200 is significantly increased, a loss of ethylene occurs and an overload occurs on a cold box CB. As a result, it is difficult to secure a circulation from the cold box CB to a deethanizer D2.

On the other hand, according to the method for preparing ethylene of the present invention, in the purification process (S4), in a case where a second heat exchanger 30 and a third gas-liquid separator 300 are used, a refrigerant in a range of −95° C. to −105° C. may be used. Accordingly, a content of methane circulated to the cold box CB is easily adjusted, which is effective in preventing an overload in the purification process.

According to an embodiment of the present invention, the first heat exchanger 20 is for cooling a feed stream containing C1 and C2 hydrocarbon compounds. As a refrigerant of the first heat exchanger 20, a part of the compressed discharge stream of the second compressor P2 which is a first circulation flow may be used as a first refrigerant stream.

Accordingly, the feed stream containing C1 and C2 hydrocarbon compounds passing through the first heat exchanger 20 may be cooled by the first heat exchanger 20. As a specific example, a temperature of the feed stream containing C1 and C2 hydrocarbon compounds before passing through the first heat exchanger 20 may be −65° C. to −55° C., −63° C. to −57° C., or −61° C. to −59° C., and a temperature of the feed stream containing C1 and C2 hydrocarbon compounds after passing through the first heat exchanger 20 may be −76° C. to −66° C., −75° C. to −68° C., or −73° C. to −71° C. According to an embodiment of the present invention, condensation of the feed stream is smoothly performed in the temperature range of the feed stream before and after passing through the first heat exchanger 20, such that an overload on the flow flowing to the cold box is prevented. As a result, process stability is improved.

According to an embodiment of the present invention, the feed stream passed through the first heat exchanger 20 and fed to the second gas-liquid separator 200 may be subjected to gas-liquid separation into a bottom discharge stream and an overhead discharge stream of the second gas-liquid separator 200 in the second gas-liquid separator 200.

According to an embodiment of the present invention, a part of the bottom discharge stream of the second gas-liquid separator 200 may be fed to the demethanizer D1 and a residue of the bottom discharge stream of the second gas-liquid separator 200 may be circulated to the deethanizer D2. The bottom discharge stream of the second gas-liquid separator 200 may contain hydrogen and C1 and C2 hydrocarbon compounds. The part of the bottom discharge stream of the second gas-liquid separator 200 to be fed to the demethanizer D1 may contain hydrogen and C1 and C2 hydrocarbon compounds, and the residue of the bottom discharge stream of the second gas-liquid separator 200 circulated to the deethanizer D2 may contain hydrogen and C1 and C2 hydrocarbon compounds.

In addition, according to an embodiment of the present invention, the overhead discharge stream of the second gas-liquid separator 200 is passed through the second heat exchanger 30 and may be fed to the third gas-liquid separator 300. According to an embodiment of the present invention, the overhead discharge stream of the second gas-liquid separator 200 may contain hydrogen and C1 and C2 hydrocarbon compounds.

According to an embodiment of the present invention, the second heat exchanger 30 is for cooling the overhead discharge stream of the second gas-liquid separator 200. As a refrigerant of the second heat exchanger 30, as described later, a part of the compressed discharge stream of the second compressor P2 which is a second circulation flow may be used as a second refrigerant stream.

Accordingly, the overhead discharge stream of the second gas-liquid separator 200 may be cooled by passing through the second heat exchanger 30. As a specific example, a temperature of the overhead discharge stream of the second gas-liquid separator 200 before passing through the second heat exchanger 30 may be −76° C. to −66° C., −75° C. to −68° C., or −73° C. to −71° C., and a temperature of the overhead discharge stream of the second gas-liquid separator 200 after passing through the second heat exchanger 30 may be −90° C. to −77° C., −87° C. to −78° C., or −85° C. to −80° C. According to an embodiment of the present invention, in a case where the temperature of the overhead discharge stream of the second gas-liquid separator 200 before and after passing through the second heat exchanger 30 is within the above range, condensation of the overhead discharge stream of the second gas-liquid separator 200 having a stream with a high methane content is smoothly performed, which is effective in improving process stability. In addition, it is possible to cope with a change in a cracking yield depending on a change in the type of feedstock due to the improvement of the process stability, such that an additional gas furnace in which a gas phase feedstock is used may be freely installed, and may be individually operated even in a case where the liquid phase decomposition step in which naphtha is used is interrupted due to maintenance of process equipment.

According to an embodiment of the present invention, the overhead discharge stream of the second gas-liquid separator 200 passed through the second heat exchanger 30 and fed to the third gas-liquid separator 300 may be subjected to gas-liquid separation into a bottom discharge stream and an overhead discharge stream of the third gas-liquid separator 300 in the third gas-liquid separator 300. Here, the overhead discharge stream of the third gas-liquid separator 300 may be circulated to the cold box CB, and the overhead discharge stream of the third gas-liquid separator 300 may contain hydrogen and a C1 hydrocarbon compound and may contain a part of a C2 hydrocarbon compound.

In this regard, as described above, in the case where the second heat exchanger 30 and the third gas-liquid separator 300 are used according to the present invention, the overhead discharge stream of the second gas-liquid separator 200 may be additionally condensed using a refrigerant in a range of −95° C. to −105° C., that is, a second refrigerant stream. By doing so, a loss of ethylene may be minimized by preventing a flow rate of the overhead discharge stream of the third gas-liquid separator 300 from being significantly increased as compared to the overhead discharge stream of the second gas-liquid separator 200 of FIG. 1, and circulation from the cold box CB to the deethanizer D2 may be secured by preventing an overload on the cold box CB.

In addition, according to an embodiment of the present invention, the demethanizer D1 is for purifying and separating hydrogen, a C1 hydrocarbon compound, and a C2 hydrocarbon compound. Specifically, the part of the bottom discharge stream of the second gas-liquid separator 200 fed to the demethanizer D1 and the bottom discharge stream of the third gas-liquid separator 300 may be purified and separated into an overhead discharge stream and a bottom discharge stream of the demethanizer D1 in the demethanizer D1.

According to an embodiment of the present invention, the overhead discharge stream of the demethanizer D1 may contain hydrogen and a C1 hydrocarbon compound, and the overhead discharge stream of the demethanizer D1 may be circulated to the cold box CB. As described above, a part of the overhead discharge stream of the demethanizer D1 circulated to the cold box CB is passed through the cold box CB, and may be discharged through a tail gas or may be circulated to the deethanizer D2 from the cold box CB. According to an embodiment of the present invention, the bottom discharge stream of the demethanizer D1 may be fed to the C2 separator SP. The bottom discharge stream of the demethanizer D1 may contain only a C2 hydrocarbon compound, and as a specific example, the bottom discharge stream of the demethanizer D1 may contain ethane and ethylene. In addition, according to an embodiment of the present invention, the part of the bottom discharge stream of the demethanizer D1 is passed through the heat exchanger and may be fed to the C2 separator SP, and a residue of the bottom discharge stream of the demethanizer D1 may be directly fed to the C2 separator SP.

In addition, according to an embodiment of the present invention, the C2 separator SP is for purifying and separating a C2 hydrocarbon compound, and specifically, the bottom discharge stream of the demethanizer D1 fed to the C2 separator SP may be purified and separated into an overhead discharge stream and a bottom discharge stream of the C2 separator SP in the C2 separator SP.

According to an embodiment of the present invention, the overhead discharge stream of the C2 separator SP may contain ethylene, and the overhead discharge stream of the C2 separator SP may be fed to the second compressor P2.

According to an embodiment of the present invention, the bottom discharge stream of the C2 separator SP may contain ethane, and the bottom discharge stream of the C2 separator SP may be circulated as the feedstock in the pyrolysis process (S1).

According to an embodiment of the present invention, the second compressor P2 is used for producing ethylene from the overhead discharge stream of the C2 separator SP, and may be a so-called ethylene refrigerant compressor (ERC). The compressed discharge stream of the second compressor P2 may include a first circulation flow, a second circulation flow, a third circulation flow, and a fourth circulation flow.

According to an embodiment of the present invention, the first circulation flow may be a flow in which a part of the compressed discharge stream of the second compressor P2 is passed through the first heat exchanger 20 and fed to the second compressor P2.

In addition, according to an embodiment of the present invention, the second circulation flow may be a flow in which a part of the compressed discharge stream of the second compressor P2 is passed through the second heat exchanger 30 and fed to the first compressor P1 and the compressed discharge stream of the first compressor P1 is fed to the second compressor P2.

In addition, according to an embodiment of the present invention, the third circulation flow may be a flow in which a part of the compressed discharge stream of the second compressor P2 is circulated to the C2 separator SP.

In addition, according to an embodiment of the present invention, the fourth circulation flow may be a flow in which a part of the compressed discharge stream of the second compressor P2 obtains ethylene as a product.

According to an embodiment of the present invention, the part of the compressed discharge stream of the second compressor P2 is passed through the first heat exchanger 20 and may be fed to the second compressor P2 as the first circulation flow. The first circulation flow may be used as the first refrigerant stream of the first heat exchanger 20 while passing through the first heat exchanger 20. In this regard, in FIG. 2, although the first heat exchanges 20 are illustrated in the front of the second gas-liquid separator 200 and the front of the second compressor P2, respectively, for convenience of description and illustration, the first heat exchange 20 provided in the front of the second gas-liquid separator 200 and the first heat exchange 20 provided in the front of the second compressor P2 may be identical to each other.

According to the method for preparing ethylene of the present invention, heat between the feed stream containing C1 and C2 hydrocarbon compounds passing through the first heat exchanger 20 and the first circulation flow may be exchanged in the first heat exchanger 20 by a counter-current flow, a co-current flow, or a cross flow. In this case, the first circulation flow is used as the first refrigerant stream and may cool the feed stream containing C1 and C2 hydrocarbon compounds.

According to an embodiment of the present invention, a temperature of the first circulation flow before passing through the first heat exchanger 20 may be −70° C. to −80° C., −72° C. to −78° C., or −74° C. to −76° C., and a temperature of the first circulation flow after passing through the first heat exchanger 20 may be −70° C. to −80° C., −72° C. to −78° C., or −74° C. to −76° C. According to an embodiment of the present invention, in a case where the temperature of the first circulation flow before and after passing through the first heat exchanger 20 is within the above range, the feed stream containing C1 and C2 hydrocarbon compounds as the first refrigerant stream is effectively condensed in terms of a condition in which the feed stream is suitably fed to the second gas-liquid separator 200.

Meanwhile, according to an embodiment of the present invention, a temperature of the part of the compressed discharge stream of the second compressor P2 forming the first circulation flow is required to be lowered to be used as the first refrigerant stream in a range of −70° C. to −80° C. before passing through the first heat exchanger 20, and the temperature may be lowered by adjusting a pressure of the part of the compressed discharge stream of the second compressor P2 forming the first circulation flow. In this case, the pressure adjustment of the part of the compressed discharge stream of the second compressor P2 forming the first circulation flow may be performed by a pressure reduction of 10 bar to 20 bar, 13 bar to 18 bar, or 14 bar to 15 bar.

In addition, according to an embodiment of the present invention, the first circulation flow after passing through the first heat exchanger 20 is joined to the overhead discharge stream of the C2 separator SP and may be fed to the second compressor P2.

In addition, according to an embodiment of the present invention, the part of the compressed discharge stream of the second compressor P2 is passed through the second heat exchanger 30 and may be fed to the first compressor P1 as the second circulation flow. The second circulation flow may be used as the second refrigerant stream of the second heat exchanger 30 while passing through the second heat exchanger 30. In this regard, in FIG. 2, although the second heat exchanges 30 are illustrated in the front of the third gas-liquid separator 300 and in the front of the first compressor P1, respectively, for convenience of description and illustration, the second heat exchange 30 provided in the front of the third gas-liquid separator 300 and the second heat exchange 30 provided in the front of the first compressor P1 may be identical to each other.

According to the method for preparing ethylene of the present invention, heat between the overhead discharge stream of the second gas-liquid separator 200 passing through the second heat exchanger 30 and the second circulation flow may be exchanged in the second heat exchanger 30 by a counter-current flow, a co-current flow, or a cross flow. In this case, the second circulation flow which is the second refrigerant stream may cool the overhead discharge stream of the second gas-liquid separator 200.

According to an embodiment of the present invention, a temperature of the second circulation flow before passing through the second heat exchanger 30 may be −95° C. to −105° C., −97° C. to −103° C., or −100° C. to −102° C., and a temperature of the second circulation flow after passing through the second heat exchanger 30 may be −95° C. to −105° C., −97° C. to −103° C., or −100° C. to −102° C. According to an embodiment of the present invention, as the second refrigerant stream, the second circulation flow before and after passing through the second heat exchanger 30 makes it possible to sufficiently condense the overhead discharge stream of the second gas-liquid separator 200 having a high methane content in the stream, within the above temperature range, which is effective in excellent process stability. In addition, it is possible to selectively use a refrigerant having a relatively lower temperature using a latent heat of ethylene, prior to obtain ethylene included in the compressed discharge stream of the second compressor P2 as a product, which is effective in improving process yield.

Meanwhile, according to an embodiment of the present invention, the temperature of the second circulation flow is required to be lowered to be used as the second refrigerant stream in a range of −95° C. to −105° C. before passing through the second heat exchanger 30. The temperature may be lowered by pressure adjustment of the part of the compressed discharge stream of the second compressor P2 forming the second circulation flow. Specifically, the first circulation stream and the second circulation stream is a flow divided from the compressed discharge stream of the second compressor P2 starting from a certain region. The part of the compressed discharge stream of the second compressor P2 as the first circulation stream is in a state in which the temperature of the part of the compressed discharge stream of the second compressor P2 is lowered to a range of −70° C. to −80° C. in order to be used as the first refrigerant stream. In this case, the second circulation flow may be formed by a simple method in which a pressure of the part of the compressed discharge stream of the second compressor P2 having a temperature with a range of −70° C. to −80° C. is adjusted again so that the temperature of the part of the compressed discharge stream of the second compressor P2 is lowered to a range of −95° C. to −105° C. The second circulation flow may be used as the second refrigerant stream. In this case, the pressure adjustment of the compressed discharge stream of the second compressor P2 having the temperature with the range of −70° C. to −80° C. may be performed by a pressure reduction of 15 bar to 25 bar, 16 bar to 20 bar, or 17 bar to 18 bar. As compared to this, practically, it is difficult to implement a case in which a separate refrigerant stream in a range of −95° C. to −105° C. is formed and fed, in order to condense the feed stream containing C1 and C2 hydrocarbon compounds. Even though a refrigerant stream in a range of −95° C. to −105° C. is formed by separating propylene from a recycled C3 hydrocarbon compound, the energy is consumed 10 times or more as compared to the energy required when forming the second refrigerant stream according to the present invention. In addition, according to an embodiment of the present invention, the first compressor P1 is for compressing the second circulation flow used as the second refrigerant stream in the second heat exchanger 30 and feeding the second circulation flow to the second compressor P2. That is, the compressed discharge stream of the first compressor P1 may be fed to the second compressor P2.

In this regard, in order for the second circulation flow used as the second refrigerant stream in the second heat exchanger 30 to be circulated to the second compressor P2 and fed, the required pressure condition needs to be satisfied. That is, since the second circulation flow to be used as the second refrigerant stream of the second heat exchanger 30 is in a press reduction state in advance in order to perform additional temperature decrease, in order to feed the second circulation flow to the second compressor P2, the pressure of the second circulation flow is required to be increased again. Accordingly, the first compressor P1 is for compressing the second circulation flow used as the second refrigerant stream in the second heat exchanger 30 in the press reduction state in advance and feeding the second circulation flow to the second compressor P2. Therefore, the compressed discharge stream of the first compressor P1 may be fed to the second compressor P2.

In addition, according to an embodiment of the present invention, the part of the compressed discharge stream of the second compressor P2 is passed through the second heat exchanger 30 and fed to the first compressor P1 as the second circulation flow. Such a stream may be formed only in a case where a content of C1 in the feed stream containing C1 and C2 hydrocarbon compounds is 35 mole % or more. For example, in a case where the content of C1 in the feed stream is 35 mole % to 45 mole %, 35 mole % to 41 mole %, or 35 mole % to 39 mole %, the part of the compressed discharge stream of the second compressor P2 is passed through the second heat exchanger 30 and fed to the first compressor P1 as the second circulation flow. As such, the fact that a content of C1 in the feed stream is high may mean that a content of methane in the feed stream is high. In this case, the part of the compressed discharge stream of the second compressor P2 is passed through the second heat exchanger 30 and fed to the first compressor P1 as the second circulation flow, such that a flow rate of the overhead discharge stream of the second gas-liquid separator 200 is prevented from being increased significantly. As a result, the overload on the cold box CB may be prevented, a loss of ethylene may be minimized, and the circulation from the cold box CB to the deethanizer D2 may be smoothly performed.

On the other hand, in a case where the content of C1 in the feed stream is less than 35 mole %, a stream in which the part of the compressed discharge stream of the second compressor P2 is passed through the second heat exchanger 30 and fed to the first compressor P1 as the second circulation may not be formed. For example, in a case where the content of C1 in the feed stream is less than 35 mole %, since the content of methane in the feed stream is low, even though the feed stream is not condensed by the second circulation flow, which is the second refrigerant stream at a lower temperature, the problem caused by the high methane content does not occur. As such, the step of passing the part of the compressed discharge stream of the second compressor P2 through the second heat exchanger 30 and feeding it to the first compressor P1 as the second circulation flow is alternatively performed depending on the content of C1 in the feed stream containing C1 and C2 hydrocarbon compounds, such that ethylene may be further effectively produced. Therefore, it is possible to save process energy.

Meanwhile, according to an embodiment of the present invention, the method for preparing ethylene may further include a process of purifying and separating a C3+ hydrocarbon compound from the pyrolysis compressed stream containing hydrogen and C1, C2, and C3+ hydrocarbon compounds which is fed from the compression process (S3), before the feed stream containing C1 and C2 hydrocarbon compounds is passed through the first heat exchanger 20 and fed to the second gas-liquid separator 200.

Specifically, the method for preparing ethylene may further include: feeding a pyrolysis compressed stream containing hydrogen and C1, C2, and C3+ hydrocarbon compounds to a deethanizer D2; feeding an overhead discharge stream of the deethanizer D2 to a third compressor P3; and feeding a compressed discharge stream of the third compressor P3 to an acetylene converter AC. A bottom discharge stream of the acetylene converter AC may be a feed stream containing C1 and C2 hydrocarbon compounds.

According to an embodiment of the present invention, the multistage compression in the compression process (S3) may be performed by four-stage compressors (a fourth compressor is represented by P3 in FIG. 2 and the first to third compressors positioned in the front of the fourth compressor are not illustrated). Specifically, in the compression process (S3), first- to third-stage compressions are performed, and the pyrolysis compressed stream containing hydrogen and C1, C2, and C3+ hydrocarbon compounds which is compressed and discharged at the third-stage compressor may be fed to the deethanizer D2 of the purification process (S4). Hydrogen, C1 and C2 hydrocarbon compounds, and a C3+ hydrocarbon compound are purified and separated in the deethanizer D2, the C3+ hydrocarbon compound is discharged to a bottom discharge stream of the deethanizer D2, the hydrogen and the C1 and C2 hydrocarbon compounds are discharged to an overhead discharge stream of the deethanizer D2, the overhead discharge stream of the deethanizer D2 is fed to the third compressor which is the fourth compressor among the four-stage compressors, and the four-stage compression may be performed in the purification process (S4).

In addition, in the purification process (S4), the pyrolysis compressed stream containing hydrogen and C1, C2, and C3+ hydrocarbon compounds may be cooled by one or more heat exchangers before being fed to the deethanizer D2, the compressed discharge stream of the third compressor P3 may be cooled by one or more heat exchangers before being fed to the acetylene converter AC, and the feed stream containing C1 and C2 hydrocarbon compounds which is a bottom discharge stream of the acetylene converter AC may be cooled by one or more heat exchangers, may be dried by one or more driers, and may be separated into a part of the stream by one or more gas-liquid separators, before being fed to the first heat exchanger 20.

According to an embodiment of the present invention, the one or more gas-liquid separators may be a first gas-liquid separator 100, the bottom discharge stream of the acetylene converter AC fed to the first gas-liquid separator 100 may be subjected to gas-liquid separation into the bottom discharge stream and the overhead discharge stream of the first gas-liquid separator 100 in the first gas-liquid separator 100.

According to an embodiment of the present invention, in a case where the first gas-liquid separator 100 is provided, the overhead discharge stream of the first gas-liquid separator 100 may be a feed stream containing C1 and C2 hydrocarbon compounds.

According to an embodiment of the present invention, in a case where the first gas-liquid separator 100 is provided, the bottom discharge stream of the first gas-liquid separator 100 may be recycled to the deethanizer D2.

In addition, according to an embodiment of the present invention, the bottom discharge stream of the deethanizer D2 may be fed to a depropanizer (not illustrated), and then a process of purifying and compressing a C3+ hydrocarbon compound may be performed in the depropanizer (not illustrated).

In addition, the present invention provides an apparatus for preparing ethylene for implementing the method for preparing ethylene (FIG. 2). The apparatus for preparing ethylene includes: a first heat exchanger 20 cooling a feed stream by using a part of a compressed discharge stream of a second compressor P2 which is a first circulation flow as a first refrigerant stream; a second gas-liquid separator 200 performing gas-liquid separation on the cooled feed stream discharged from the first heat exchanger 20; a second heat exchanger 30 cooling an overhead discharge stream of the second gas-liquid separator 200 by using a part of the compressed discharge stream of the second compressor P2 which is a second circulation flow as a second refrigerant stream; a third gas-liquid separator 300 performing gas-liquid separation on the cooled overhead discharge stream of the second gas-liquid separator 200 discharged from the second heat exchanger 30; a demethanizer D1 separating methane from a bottom discharge stream of the second gas-liquid separator 200 and a bottom discharge stream of the third gas-liquid separator 300; a C2 separator SP separating C2 from a bottom discharge stream of the demethanizer D1; a first compressor P1 compressing the second circulation flow used as the refrigerant in the second heat exchanger 30; and a second compressor P2 compressing an overhead discharge stream of the C2 separator SP, the first circulation flow, and a compressed discharge stream of the first compressor P1.

In addition, according to an embodiment of the present invention, the apparatus for preparing ethylene may further include: a deethanizer D2 separating a C3+ hydrocarbon compound from a pyrolysis compressed stream containing hydrogen and C1, C2, and C3+ hydrocarbon compounds; a third compressor P3 compressing an overhead discharge stream of the deethanizer D2; and an acetylene converter AC converting acetylene from a compressed discharge stream of the third compressor into ethylene.

In addition, according to an embodiment of the present invention, the second gas-liquid separator 200 may perform gas-liquid separation on the bottom discharge stream containing hydrogen and C1 and C2 hydrocarbon compounds and the overhead discharge stream containing hydrogen and C1 and C2 hydrocarbon compounds.

In addition, according to an embodiment of the present invention, the third gas-liquid separator 300 may perform gas-liquid separation on the bottom discharge stream containing hydrogen and C1 and C2 hydrocarbon compounds and the overhead discharge stream containing hydrogen and a C1 hydrocarbon compound.

Respective apparatuses of the apparatus for preparing ethylene according to the present invention may be an apparatus for implementing processes according to the method for preparing ethylene described above.

Hereinabove, the method for preparing ethylene according to the present invention has been described and illustrated in the drawing. However, the description and the illustration of the drawing are for only essential components for understating the present invention, and processes and apparatuses not separately described and illustrated may be properly applicable and used for implementing the method for preparing ethylene, in addition to the processes and apparatuses described and illustrated in the drawing.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXPERIMENTAL EXAMPLES

Example 1

The processes of the process flow diagram illustrated in FIG. 2 were simulated using the ASPEN Plus simulator produced by Aspen Technology, Inc.

As a feedstock of the pyrolysis process (S1), a recycled C2 hydrocarbon compound with a flow rate of 32,740 kg/hr, a recycled C3 hydrocarbon compound with a flow rate of 16,180 kg/hr, and propane supplied from the outside with a flow rate of 75,561 kg/hr (a content of C3 in the total feedstock: 74.7 wt %) were used. The composition of the pyrolysis compressed stream is shown in Table 1, the temperatures and pressures of the respective streams in the purification process (S4) are shown in Table 2, and the composition of the overhead discharge stream and the flow rate of the third gas-liquid separator 300 are shown in Table 3.

TABLE 1

| Classification | Content (mole %) |
|---|---|
| Hydrogen | 20.4 |
| Methane | 26.0 |
| Ethane | 7.6 |
| Ethylene | 31.4 |
| Acetylene | 0.4 |
| Propane | 5.7 |
| Propylene | 6.5 |
| C4+ | 2.0 |

TABLE 2

| Classification | Temperature (° C.) | Pressure (kg/cm$^2$G) |
|---|---|---|
| Pyrolysis compressed stream containing hydrogen and C1, C2, and C3+ hydrocarbon compounds | −37.0 | 7.35 |
| Overhead discharge stream of deethanizer D2 | −68.0 | 7.21 |
| Compressed discharge stream of third compressor P3 | 31.0 | 28.54 |
| Bottom discharge stream of acetylene converter AC | 77.7 | 25.29 |
| Feed stream containing C1 and C2 hydrocarbon compounds before passing through first heat exchanger 20 | −60.0 | 23.36 |
| Feed stream containing C1 and C2 hydrocarbon compounds after passing through first heat exchanger 20 | −72.0 | 23.05 |
| Bottom discharge stream of second gas-liquid separator 200 | −72.2 | 22.84 |
| Overhead discharge stream of second gas-liquid separator 200 before passing through second heat exchanger 30 | −72.2 | 22.84 |
| Overhead discharge stream of second gas-liquid separator 200 after passing through second heat exchanger 30 | −82.6 | 22.64 |
| Overhead discharge stream of third gas-liquid separator 300 | −82.7 | 22.50 |
| Bottom discharge stream of third gas-liquid separator 300 | −82.7 | 22.50 |
| Overhead discharge stream of demethanizer D1 | −83.7 | 9.30 |
| Bottom discharge stream of demethanizer D1 | −47.3 | 9.60 |
| Overhead discharge stream of C2 separator SP | −73.9 | 3.47 |
| Bottom discharge stream of C2 separator SP | −52.6 | 4.10 |
| Compressed discharge stream of second compressor P2 | −58.7 | 18.00 |
| First circulation flow before passing through first heat exchanger 20 (first refrigerant stream) | −74.6 | 3.34 |
| First circulation flow after passing through first heat exchanger 20 (first refrigerant stream) | −74.9 | 3.30 |
| Second circulation flow before passing through second heat exchanger 30 (second refrigerant stream) | −100.9 | 0.20 |
| Second circulation flow after passing through second heat exchanger 30 (second refrigerant stream) | −101.5 | 0.16 |

TABLE 2-continued

| Classification | Temperature (° C.) | Pressure (kg/cm²G) |
|---|---|---|
| Compressed discharge stream of first compressor P1 | −25.4 | 3.30 |

TABLE 3

| Classification | Content (mole %) |
|---|---|
| Hydrogen | 28.0 |
| Methane | 58.8 |
| Ethane | 11.9 |
| Ethylene | 1.3 |
| Flow rate | 57,547 (kg/hr) |

Example 2

The process of the process flow diagram illustrated in FIG. 2 was simulated using the ASPEN Plus simulator produced by Aspen Technology, Inc.

As a feedstock of the pyrolysis process (S1), a recycled C2 hydrocarbon compound with a flow rate of 7,920 kg/hr, a recycled C3 hydrocarbon compound with a flow rate of 18,275 kg/hr, and propane supplied from the outside with a flow rate of 103,810 kg/hr (a content of C3 in the total feedstock: 93.9 wt %) were used. The composition of the pyrolysis compressed stream is shown in Table 4, the temperatures and pressures of the respective streams in the purification process (S4) are shown in Table 5, and the composition of the overhead discharge stream and the flow rate of the third gas-liquid separator 300 are shown in Table 6.

TABLE 4

| Classification | Content (mole %) |
|---|---|
| Hydrogen | 17.7 |
| Methane | 29.1 |
| Ethane | 4.7 |
| Ethylene | 30.1 |
| Acetylene | 0.5 |
| Propane | 7.4 |
| Propylene | 7.3 |
| C4+ | 0 |

TABLE 5

| Classification | Temperature (° C.) | Pressure (kg/cm²G) |
|---|---|---|
| Pyrolysis compressed stream containing hydrogen and C1, C2, and C3+ hydrocarbon compounds | −21 | 7.5 |
| Overhead discharge stream of deethanizer D2 | −72 | 7.21 |
| Compressed discharge stream of third compressor P3 | 34.4 | 28.54 |
| Bottom discharge stream of acetylene converter AC | 77.7 | 85.29 |
| Feed stream containing C1 and C2 hydrocarbon compounds before passing through first heat exchanger 20 | −55.6 | 23.36 |
| Feed stream containing C1 and C2 hydrocarbon compounds after passing through first heat exchanger 20 | −72.2 | 22.84 |
| Bottom discharge stream of second gas-liquid separator 200 | −72.2 | 22.84 |
| Overhead discharge stream of second gas-liquid separator 200 before passing through second heat exchanger 30 | −72.2 | 22.84 |
| Overhead discharge stream of second gas-liquid separator 200 after passing through second heat exchanger 30 | −80.2 | 22.64 |
| Overhead discharge stream of third gas-liquid separator 300 | −80.3 | 22.50 |
| Bottom discharge stream of third gas-liquid separator 300 | −80.3 | 22.50 |
| Overhead discharge stream of demethanizer D1 | −68.1 | 9.30 |
| Bottom discharge stream of demethanizer D1 | −48.3 | 9.60 |
| Overhead discharge stream of C2 separator SP | −73.9 | 3.47 |
| Bottom discharge stream of C2 separator SP | −52.6 | 4.10 |
| Compressed discharge stream of second compressor P2 | −58.7 | 18.00 |
| First circulation flow before passing through first heat exchanger 20 (first refrigerant stream) | −74.6 | 3.34 |
| First circulation flow after passing through first heat exchanger 20 (first refrigerant stream) | −74.9 | 3.30 |
| Second circulation flow before passing through second heat exchanger 30 (second refrigerant stream) | −100.9 | 0.20 |
| Second circulation flow after passing through second heat exchanger 30 (second refrigerant stream) | −101.5 | 0.16 |
| Compressed discharge stream of first compressor P1 | −25.4 | 3.30 |

TABLE 6

| Classification | Content (mole %) |
|---|---|
| Hydrogen | 21.3 |
| Methane | 64.7 |
| Ethane | 0.9 |
| Ethylene | 13.1 |
| Flow rate | 66,730 (kg/hr) |

Comparative Example

The processes were simulated under the same conditions as in Example 1, except that the process flow diagram illustrated in FIG. 1 was used instead of the process flow diagram illustrated in FIG. 2. The composition of the pyrolysis compressed stream is the same as shown in Table 1.

The temperatures and pressures of the respective streams in the purification process (S4) are shown in Table 7 and the composition and the flow rate of the overhead discharge stream of the second gas-liquid separator 200 are shown in Table 8.

TABLE 7

| Classification | Temperature (° C.) | Pressure (kg/cm$^2$G) |
| --- | --- | --- |
| Pyrolysis compressed stream containing hydrogen and C1, C2, and C3+ hydrocarbon compounds | −21 | 7.5 |
| Overhead discharge stream of deethanizer D2 | −67.8 | 7.21 |
| Compressed discharge stream of third compressor P3 | 35.8 | 28.54 |
| Bottom discharge stream of acetylene converter AC | 77.7 | 25.29 |
| Feed stream containing C1 and C2 hydrocarbon compounds before passing through first heat exchanger 20 | −64.6 | 23.36 |
| Feed stream containing C1 and C2 hydrocarbon compounds after passing through first heat exchanger 20 | −80.9 | 23.05 |
| Bottom discharge stream of second gas-liquid separator 200 | −81.0 | 22.91 |
| Overhead discharge stream of second gas-liquid separator 200 | −81.0 | 22.91 |
| Overhead discharge stream of demethanizer D1 | −91.2 | 9.3 |
| Bottom discharge stream of demethanizer D1 | −53.3 | 9.6 |
| Overhead discharge stream of C2 separator SP | −74.2 | 3.47 |
| Bottom discharge stream of C2 separator SP | −52.5 | 4.1 |
| Compressed discharge stream of second compressor P2 | 27.5 | 18.85 |
| First circulation flow before passing through first heat exchanger 20 (first refrigerant stream) | −70.6 | 4.3 |
| First circulation flow after passing through first heat exchanger 20 (first refrigerant stream) | −66.6 | 4.15 |

TABLE 8

| Classification | Content (mole %) |
| --- | --- |
| Hydrogen | 30.8 |
| Methane | 56.5 |
| Ethane | 1.1 |
| Ethylene | 11.6 |
| Flow rate | 50,464 (kg/hr) |

As shown in Tables 1 and 7, it was confirmed that in a case where, in the pyrolysis process (S1), a flow rate of propane which is used as a feedstock is increased, the content of methane in the pyrolysis compressed stream was increased. As shown in Tables 3 and 8, it was confirmed that in a case where the feedstocks of the same type are fed at the same flow rates, in the purification process (S4), as compared to Comparative Example in which only the second gas-liquid separator 200 is used, in Example 1 in which the third gas-liquid separator 300 is used after performing additional cooling using a refrigerant in a range of −95° C. to −105° C. through the second heat exchanger 30, it was possible to decrease the content of ethylene contained in the overhead discharge stream of each of the gas-liquid separators 100 and 200 circulated to the cold box CB, such that the loss of ethylene and the overload on the cold box CB were prevented and the circulation from the cold box CB to the deethanizer D2 was secured.

In addition, as shown in Tables 1 to 4, it was confirmed that in a case where, in the pyrolysis process (S1), in the feedstock, a content and proportion of propane fed from the outside was increased further, the content of methane in the pyrolysis compressed stream was increased further. As shown in Tables 5 and 6, it was confirmed that, by using the third gas-liquid separator 300 after performing additional cooling using a refrigerant in a range of −95° C. to −105° C. through the second heat exchanger 30, such that the purification process (S4) was normally performed even though the content and proportion of propane which is used as a feedstock was increased.

Meanwhile, the temperature and the pressure of each of the stream shown in Table 7 correspond to a temperature and a pressure for performing the process simulation according to the process flow diagram illustrated in FIG. 1. However, in a case of the feed stream containing C1 and C2 hydrocarbon compounds after passing through the first heat exchanger 20 of Table 7, since the actual process is performed in a system in which the lowest temperature is −75° C., the process cannot be performed at −80.9° C. Accordingly, since the feed stream containing C1 and C2 hydrocarbon compounds to be fed to the second gas-liquid separator 200 after passing through the first heat exchanger 20 is not sufficiently condensed, the purification of the bottom discharge stream and the overhead discharge stream of the second gas-liquid separator 200 are also not performed at the above temperature and the pressure.

Therefore, in a case where the process flow diagram illustrated in FIG. 1 is applied in a real process rather than the simulation in which conditions that the process can be operated are set, there is problem in that the condensation in the first heat exchanger 20 is not sufficient, and the non-condensed fluid is discharged together with the overhead discharge stream of the second gas-liquid separator 200 and is introduced into the cold box CB. In addition, the cold box CB lacks energy for performing the cooling circulation due to the fluid introduced into the cold box CB. Thus, a serious loss in which ethylene which is a product is discharged through a tail gas occurs. In addition, the amount of fluid reintroduced into the third compressor P3 is increased by Joule-Thomson recycle in the cold box CB, therefore the amount of work is increased, resulting in the occurrence of the overload over the entire cold box CB.

The inventors of the present invention was found from the above results that in a case where ethylene is produced according to the present invention, it is possible to cope with a change in a cracking yield depending on a change in the type of feedstock, such that an additional gas furnace in which a gas phase feedstock is used may be freely installed, and may be individually operated even in a case where the liquid phase decomposition step in which naphtha is used is interrupted due to maintenance of process equipment.

The invention claimed is:
1. A method for preparing ethylene comprising:
passing a feed stream containing C1 and C2 hydrocarbon compounds through a first heat exchanger and feeding the feed stream passed through the first heat exchanger to a second gas-liquid separator;
feeding a part of a bottom discharge stream of the second gas-liquid separator to a demethanizer, passing an overhead discharge stream of the second gas-liquid separator through a second heat exchanger, and feeding the overhead discharge stream of the second gas-liquid separator passed through the second heat exchanger to a third gas-liquid separator;

feeding a bottom discharge stream of the third gas-liquid separator to the demethanizer;
feeding a bottom discharge stream of the demethanizer to a C2 separator;
feeding an overhead discharge stream of the C2 separator to a second compressor;
passing a first part of a compressed discharge stream of the second compressor through the first heat exchanger and feeding the first part of the compressed discharge stream of the second compressor passed through the first heat exchanger to the second compressor as a first circulation flow;
passing a second part of the compressed discharge stream of the second compressor through the second heat exchanger and feeding the second part of the compressed discharge stream of the second compressor passed through the second heat exchanger to a first compressor as a second circulation flow; and
feeding a compressed discharge stream of the first compressor to the second compressor.

2. A method for preparing ethylene comprising:
passing a feed stream containing C1 and C2 hydrocarbon compounds through a first heat exchanger and feeding the feed stream passed through the first heat exchanger to a second gas-liquid separator;
feeding a part of a bottom discharge stream of the second gas-liquid separator to a demethanizer, passing an overhead discharge stream of the second gas-liquid separator through a second heat exchanger, and feeding the overhead discharge stream of the second gas-liquid separator passed through the second heat exchanger to a third gas-liquid separator;
feeding a bottom discharge stream of the third gas-liquid separator to the demethanizer;
feeding a bottom discharge stream of the demethanizer to a C2 separator;
feeding an overhead discharge stream of the C2 separator to a second compressor;
passing a first part of a compressed discharge stream of the second compressor through the first heat exchanger and feeding the first part of the compressed discharge stream of the second compressor passed through the first heat exchanger to the second compressor as a first circulation flow;
passing a second part of the compressed discharge stream of the second compressor through the second heat exchanger when a content of C1 hydrocarbon compounds in the feed stream containing the C1 and C2 hydrocarbon compounds is 35 mole % or more and feeding the second part of the compressed discharge stream of the second compressor passed through the second heat exchanger to a first compressor as a second circulation flow; and
feeding a compressed discharge stream of the first compressor to the second compressor.

3. The method for preparing ethylene of claim 2, wherein a temperature of the feed stream containing the C1 and C2 hydrocarbon compounds before passing through the first heat exchanger is −65° C. to −55° C., and a temperature of the feed stream containing the C1 and C2 hydrocarbon compounds after passing through the first heat exchanger is −76° C. to −66° C.

4. The method for preparing ethylene of claim 2, wherein a residue of the bottom discharge stream of the second gas-liquid separator is fed to a deethanizer.

5. The method for preparing ethylene of claim 2, wherein the overhead discharge stream of the second gas-liquid separator contains hydrogen and C1 and C2 hydrocarbon compounds.

6. The method for preparing ethylene of claim 2, wherein a temperature of the overhead discharge stream of the second gas-liquid separator before passing through the second heat exchanger is −76° C. to −66° C., and a temperature of the overhead discharge stream of the second gas-liquid separator after passing through the second heat exchanger is −90° C. to −77° C.

7. The method for preparing ethylene of claim 2, wherein an overhead discharge stream of the third gas-liquid separator is circulated to a cold box.

8. The method for preparing ethylene of claim 2, wherein an overhead discharge stream of the demethanizer is circulated to a cold box.

9. The method for preparing ethylene of claim 2, wherein the overhead discharge stream of the C2 separator contains ethylene.

10. The method for preparing ethylene of claim 2, wherein a bottom discharge stream of the C2 separator is circulated as a feedstock.

11. The method for preparing ethylene of claim 2, wherein a part of the compressed discharge stream of the second compressor is circulated to the C2 separator as a third circulation flow.

12. The method for preparing ethylene of claim 2, wherein a temperature of the first circulation flow before passing through the first heat exchanger is −70° C. to −80° C., and a temperature of the first circulation flow after passing through the first heat exchanger is −70° C. to −80° C.

13. The method for preparing ethylene of claim 2, wherein a temperature of the second circulation flow before passing through the second heat exchanger is −95° C. to −105° C., and a temperature of the second circulation flow after passing through the second heat exchanger is −95° C. to −105° C.

14. The method for preparing ethylene of claim 2, wherein a stream of the first circulation flow after passing through the first heat exchanger is joined with the overhead discharge stream of the C2 separator and the joined stream is fed to the second compressor.

15. The method for preparing ethylene of claim 2, further comprising:
feeding a pyrolysis compressed stream containing hydrogen and C1, C2, and C3+ hydrocarbon compounds to a deethanizer;
feeding an overhead discharge stream of the deethanizer to a third compressor; and
feeding a compressed discharge stream of the third compressor to an acetylene converter,
wherein a bottom discharge stream of the acetylene converter is a feed stream containing C1 and C2 hydrocarbon compounds.

16. The method for preparing ethylene of claim 15, wherein a bottom discharge stream of the deethanizer is fed to a depropanizer.

17. An apparatus for preparing ethylene comprising:
a first heat exchanger comprising a first refrigerant stream, wherein the first refrigerant stream comprises a first part of a compressed discharge stream of a second compressor, and wherein the feed stream is cooled in the first heat exchanger;
a second gas-liquid separator, wherein the cooled feed stream discharged from the first heat exchanger is gas-liquid separated in the second gas-liquid separator;

a second heat exchanger comprising a second refrigerant stream, wherein the second refrigerant stream comprises a second part of the compressed discharge stream of the second compressor, and wherein an overhead discharge stream of the second gas-liquid separator is cooled in the second heat exchanger;

a third gas-liquid separator, wherein the cooled overhead discharge stream of the second gas-liquid separator discharged from the second heat exchanger is gas-liquid separated in the third gas-liquid separator;

a demethanizer, wherein methane is separated from a bottom discharge stream of the second gas-liquid separator and a bottom discharge stream of the third gas-liquid separator in the demethanizer;

a C2 separator, wherein C2 compounds are separated from a bottom discharge stream of the demethanizer in the C2 separator;

a first compressor, wherein the second part of the compressed discharge stream of the second compressor passed through the second heat exchanger is compressed in the first compressor; and a second compressor, wherein an overhead discharge stream of the C2 separator, the first part of the compressed discharge stream of the second compressor passed through the first heat exchanger, and a compressed discharge stream of the first compressor are compressed in the second compressor.

18. The apparatus for preparing ethylene of claim 17, further comprising:

a deethanizer, wherein a C3+ hydrocarbon compound is separated from a pyrolysis compressed stream containing hydrogen and C1, C2, and C3+ hydrocarbon compounds in the deethanizer;

a third compressor, wherein an overhead discharge stream of the deethanizer is compressed in the third compressor; and an acetylene converter, wherein acetylene from a compressed discharge stream of the third compressor is converted into ethylene in the acetylene converter.

19. The apparatus for preparing ethylene of claim 17, wherein the bottom discharge stream containing hydrogen and C1 and C2 hydrocarbon compounds and the overhead discharge stream containing hydrogen and C1 and C2 hydrocarbon compounds are gas-liquid separated in the second gas-liquid separator.

20. The apparatus for preparing ethylene of claim 17, wherein separation on the bottom discharge stream containing hydrogen and C1 and C2 hydrocarbon compounds and the overhead discharge stream containing hydrogen and a C1 hydrocarbon compound are gas-liquid separated in the third gas-liquid separator.

* * * * *